(12) United States Patent
Hummel

(10) Patent No.: US 8,956,044 B2
(45) Date of Patent: Feb. 17, 2015

(54) METHOD OF ACQUIRING AN X-RAY IMAGE AND X-RAY ACQUISITION DEVICE COMPRISING AUTOMATIC WEDGE POSITIONING

(75) Inventor: Erik Hummel, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 386 days.

(21) Appl. No.: 13/266,266

(22) PCT Filed: Apr. 28, 2010

(86) PCT No.: PCT/IB2010/051853
§ 371 (c)(1),
(2), (4) Date: Oct. 26, 2011

(87) PCT Pub. No.: WO2010/128431
PCT Pub. Date: Nov. 11, 2010

(65) Prior Publication Data
US 2012/0045034 A1  Feb. 23, 2012

(30) Foreign Application Priority Data
May 5, 2009 (EP) .................................. 09159367

(51) Int. Cl.
*G21K 1/04* (2006.01)
*G21K 3/00* (2006.01)
(Continued)

(52) U.S. Cl.
CPC . *A61B 6/06* (2013.01); *A61B 6/469* (2013.01); *A61B 6/542* (2013.01); *A61B 6/4035* (2013.01)
USPC .............. 378/205; 378/95; 378/150; 378/156

(58) Field of Classification Search
USPC ........... 378/4–20, 91, 95, 147, 150, 151, 156, 378/204, 205, 210, 901
See application file for complete search history.

(56) References Cited

U.S. PATENT DOCUMENTS 5,307,396 A * 4/1994 Tsuchino .................. 378/146
5,369,678 A   11/1994 Chiu et al.
(Continued)

FOREIGN PATENT DOCUMENTS

JP  2006014822 A  1/2006
WO  2004008968 A1  1/2004
(Continued)

OTHER PUBLICATIONS

Rudin, S., Bednarek, D. R., Yang, C.-Y. J., Real-time equalization of region-of-interest fluoroscopic images using binary masks, Medical Physics 26:(7), pp. 1359-1364, 1999.
(Continued)

*Primary Examiner* — Anastasia Midkiff

(57) ABSTRACT

For acquiring an image of a moving region of interest of an object, a corresponding X-ray image acquisition apparatus may include a semitransparent X-ray transmitting device comprised in a collimator which is positioned within a beam of irradiating X-rays thereby at least partly shielding regions on a surface of a detector. After acquiring an X-ray image by detecting X-rays transmitted through the object, the position of the device is automatically adjusted based on image information included in the at least partly shielded region on the detector surface. Taking into account X-ray absorption properties of the device, a virtual image may be calculated, the virtual image corresponding to an X-ray image as if there was no X-ray absorption within the collimator. From this virtual image, the region of interest may be derived, and wedges of said device may be positioned to continuously follow the region of interest.

20 Claims, 1 Drawing Sheet

(51) Int. Cl.
*H05G 1/02* (2006.01)
*A61B 6/00* (2006.01)
*A61B 6/06* (2006.01)

(56) References Cited

U.S. PATENT DOCUMENTS

| | | | |
|---|---|---|---|
| 6,055,295 | A | 4/2000 | Murthy et al. |
| 6,480,570 | B1 * | 11/2002 | Ikeda ........................ 378/98.7 |
| 6,501,828 | B1 | 12/2002 | Popescu |
| 7,242,749 | B2 | 7/2007 | Hsieh et al. |
| 7,340,033 | B2 | 3/2008 | Mollus et al. |
| 7,409,034 | B2 * | 8/2008 | Gohno ........................... 378/7 |
| 7,597,474 | B2 | 10/2009 | Baumann |
| 2001/0050974 | A1 | 12/2001 | Schmitz |
| 2003/0076927 | A1 | 4/2003 | Nakashima |
| 2004/0008968 | A1 | 1/2004 | Lee et al. |
| 2006/0104420 | A1 * | 5/2006 | Mollus ......................... 378/147 |
| 2006/0203966 | A1 | 9/2006 | Mollus et al. |
| 2008/0056608 | A1 | 3/2008 | Spahn |
| 2011/0182492 | A1 * | 7/2011 | Grass et al. .................. 382/131 |
| 2013/0112897 | A1 | 5/2013 | Eckhoff et al. |

FOREIGN PATENT DOCUMENTS

| | | | | |
|---|---|---|---|---|
| WO | WO 2009063353 A2 * | 5/2009 | ............ | G21K 3/00 |
| WO | WO 2013/052556 A2 | 4/2013 | | |

OTHER PUBLICATIONS

Robert, N., Komljenovic, P.T., Rowlands, J.A., A filtering method for signal equalization in region-of-interest fluoroscopy, Medical Physics 29:(5), pp. 736-747, 2002.

Court, LE, Dong, L; Lee, AK; Cheung, R.; Bonnen, MD; O'Daniel, J.; Wang, H.; Mohan, R; Kuban, D., An Automatic CT-guided adaptive radiation therapy technique by online modification of multileaf collimator leaf positions for prostate cancer, International Journal of Radiation Oncology Biology Physics 62 (1):154-163, May 1, 2005.

"Radiation protection", http://en.wikipedia.org/wiki/Radiation_protection (May 20, 2014), pp. 1-11.

* cited by examiner

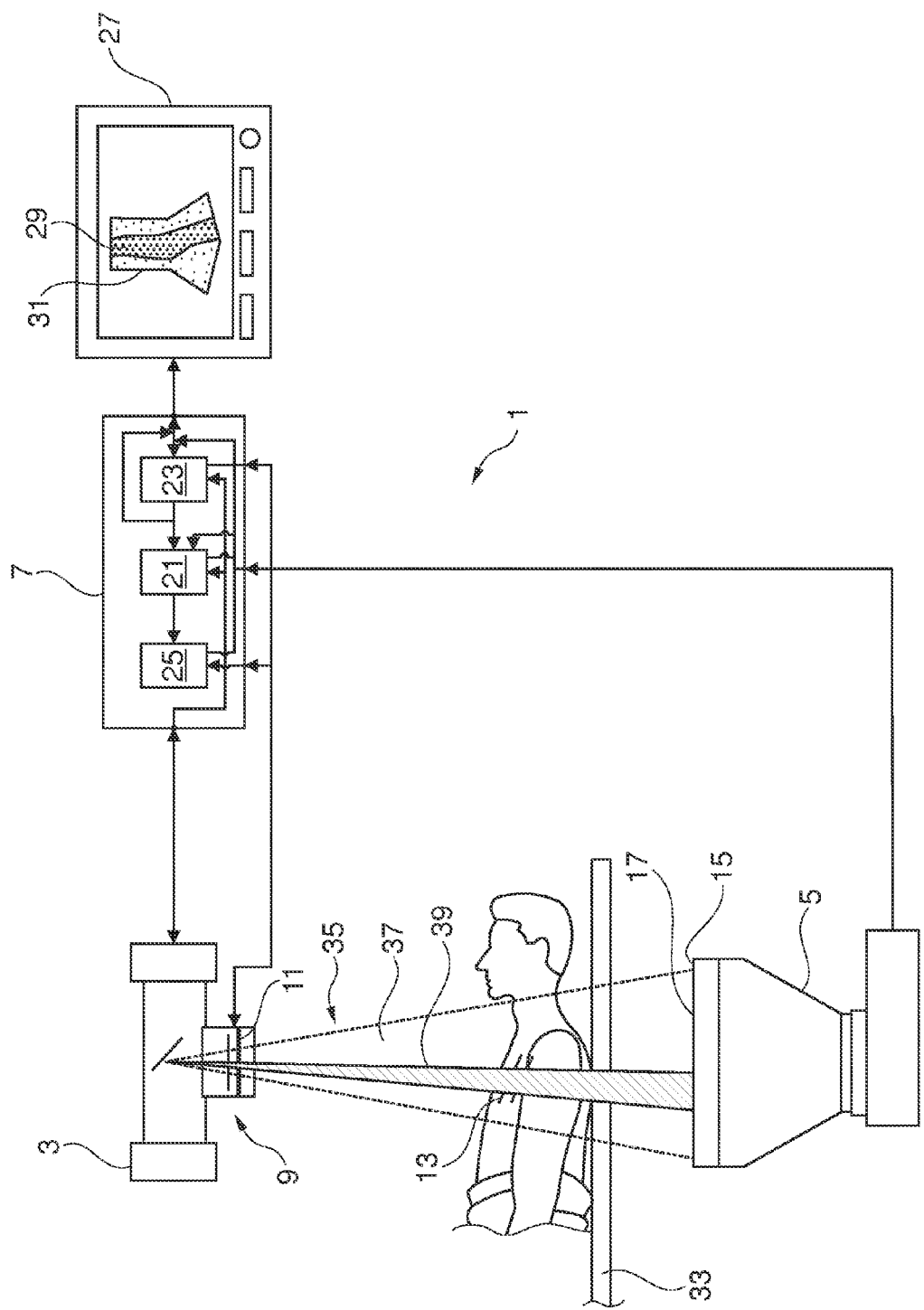

METHOD OF ACQUIRING AN X-RAY IMAGE AND X-RAY ACQUISITION DEVICE COMPRISING AUTOMATIC WEDGE POSITIONING

FIELD OF THE INVENTION

The present invention relates to a method of acquiring an X-ray image of a region of interest of an object by irradiating X-rays to the object and detecting X-rays transmitted through the object on a detector surface. Furthermore, the present invention relates to an X-ray image acquisition device and to a computer program element adapted to perform such image acquisition method.

BACKGROUND OF THE INVENTION

In X-ray image acquisition, X-rays emitted from an X-ray source are usually directed to an object to be examined and X-rays transmitted through and partly absorbed within the object are then detected on a detection surface of an X-ray detector.

Conventionally, an X-ray image acquisition device comprises a collimator. The collimator may comprise non-transparent closure parts for completely blocking portions of an X-ray beam coming from the X-ray source. Furthermore, a semitransparent X-ray transmitting device for example in the form of semitransparent diaphragm wedges may be provided. The non-transparent closure parts and the semitransparent X-ray transmitting device may enable to shape the X-ray beam coming from the X-ray source in such a way that only parts of a patient's body that are of interest are irradiated with a desired radiation intensity. Furthermore, the collimator may comprise filter elements in order to vary the spectrum of the beam in a desired way.

Using a collimator may lead to several advantages such as improving an image quality, reducing a risk of radiation damage to a patient and reducing of scattered radiation to which for example staff is exposed during image recording. In this context, the reduction in radiation exposure might be important particular in view of prolonged diagnostic and therapeutic interventions accompanied by X-ray fluoroscope observations that are increasingly taking place.

Conventionally, the collimator and in particular the semitransparent wedges have been predominantly adjusted manually by the attendant staff. However, this is not only cumbersome but may also distract from e.g. the actual surgery activity.

In order to simplify the utilization of adjustment possibilities of a collimator of an X-ray image acquisition device, U.S. Pat. No. 7,340,033, which is assigned to the same applicant as the present application, discloses an X-ray unit for generating imaging of a body comprising an automatically adjustable collimator including diaphragm and filter elements for limiting, locally attenuating and/or filtering an X-ray beam output from an X-ray source. Therein, the X-ray unit further comprises a data processing unit coupled to the collimator and designed to localize a region of interest inside a body and to transmit commands to the collimator to adjust the diaphragm and filter elements of the collimator in accordance with a restriction of subsequent X-ray beams to a localized region of interest.

The automatic adjustment of the collimator and, in particular, the automatic positioning of a semitransparent wedge usually requires a determination of an optimum position of the wedges based on some detected region of interest which shall be examined and to which the X-ray beam may be collimated. In order to be able to automatically detect a region of interest it might be necessary to use an automatic feature detection algorithm. A preliminary X-ray image may be acquired for example with a non-restricted X-ray beam and the automatic feature detection algorithm may detect a region of interest within the acquired image. Knowing the location of the region of interest, an optimum wedge position might be calculated and sent to the collimator. Thus, the wedge may be positioned such that portions of the X-rays from the X-ray source which would be transmitted through the examined object outside the region of interest are at least partly attenuated. Thereby, for example the overall X-ray dose to a patient might be reduced.

However, after wedge positioning, the automatic feature detection may not be able to detect the features of the region of interest any more. It may happen that the object to be examined changes its position with respect to the X-ray image acquisition device after such initial wedge positioning. For example, a patient to be examined might move or a table, on which the patient lies, might move with respect to the X-ray image acquisition device. Accordingly, even though the collimator and the wedges have been initially correctly positioned, such positioning might not be convenient any more during the actual observation, for example during a prolonged diagnostic or therapeutic intervention. Accordingly, the X-ray beam might not be collimated to the region of interest at all times thereby for example preventing correct image acquisition or deteriorating image quality.

SUMMARY OF THE INVENTION

Accordingly, there may be a need for a method of acquiring an X-ray image and for an X-ray image acquisition device which may improve the collimation of X-rays during an X-ray examination procedure. Furthermore, there may be a need for a computer program element adapted for controlling such image acquisition method as well as for a computer-readable medium comprising such computer program element.

Such need may be met with the subject-matter of the independent claims. Advantageous embodiments are comprised in the dependent claims.

According to a first aspect of the present invention, a method of acquiring an X-ray image of a region of interest of an object by irradiating X-rays to the object and detecting on a detector surface X-rays transmitted through the object is proposed. The method comprises a step of positioning a semitransparent X-ray transmitting device into a beam of the irradiating X-rays. Thereby, regions of the detector surface are at least partly shielded from X-rays. Then, an X-ray image is acquired by detecting X-rays transmitted through the object on the detector surface. Then, the position of the semitransparent X-ray transmitting device is automatically adjusted based on image information included in the at least partly shielded regions on the detector surface.

According to a second aspect of the present invention, an X-ray image acquisition device is proposed. The device comprises an X-ray source for generating an X-ray beam, an adjustable semitransparent X-ray transmitting device positioned within a path of the X-ray beam, an X-ray detector and a control device for adjusting a position of the semitransparent X-ray transmitting device. Therein, the X-ray image acquisition device is adapted for performing the method according to the above first aspect of the invention. In other words, the control device may be adapted for automatically adjusting the position of the semitransparent X-ray transmitting device based on image information included in a previously acquired X-ray image in regions which are at least partly shielded by a previously positioned semitransparent X-ray transmitting device.

According to a third aspect of the present invention, a computer program element is provided which, when executed on a processor, may control the method according to the above first aspect of the invention. In other words, the computer program element may command the processor such that an adjusted position of the semitransparent X-ray transmitting device may be automatically calculated based on information included in the regions on the detector surface at least partly shielded by the previously positioned semitransparent X-ray transmitting device.

According to a fourth aspect of the present invention, a computer-readable medium having the computer program element according to the third aspect of the invention stored thereon is provided.

In the following, a semitransparent X-ray transmitting device may be understood as a device having specific X-ray absorption properties. The X-ray absorption properties may vary locally along the device and may for example depend on a material and on a thickness of the semitransparent X-ray transmitting device at a specific location. In one specific example, the semitransparent X-ray transmitting device is provided as a wedge made from an X-ray attenuating material such that the X-ray absorption properties of the wedge increase with increasing thickness of the wedge. In the following description, the semitransparent X-ray transmitting device will be sometimes simply referred to as "wedge" or "semitransparent device". However, it is to be noted that such "wedge" is only a specific type of semitransparent X-ray transmitting device and any other type comprising different materials or geometries may be used alternatively.

Ideas of the present invention may be seen as based on the following recognition:

Conventionally, automatic wedge positioning, also sometimes referred o as AWP, is a method to determine an optimum position of wedges based on some detected region of interest. In such method, the optimum position may be for example calculated in such a way that a maximum area of an irradiated region outside the region of interest is covered with the wedges. It can even be allowed to cover some of the region of interest.

The region of interest may be detected automatically by a specific feature detection algorithm which may be adapted for deriving the region of interest from an acquired X-ray image. The feature detection may be application dependent and may be for example based on a detection of direct radiation or on lung-field areas in an X-ray image. The wedges may be positioned automatically based on the detected region of interest.

As indicated above, the automatic feature detection may not be possible any more subsequent to an initial placement of the wedges. This may be the case for example in direct radiation or lung-field detection as, with the wedges initially positioned, the regions corresponding to the direct radiation or to the lung-field areas are at least partly shielded from incoming X-rays such that these regions are not detectable any more on subsequent X-ray images. Accordingly, after initially setting the position of the wedges in an optimum way, it might not be possible to further detect a region of interest in subsequent images with conventional image acquisition methods.

An idea of the present invention may be to adjust the position of the wedge automatically based on image information included in the regions on the detector surface partly shielded by the initially positioned wedge. In other words, it may be the image information provided by the X-ray detector in a region where the detected X-rays had to previously pass through the wedge which image information may be used to determine an adjusted position of the wedge automatically. As described with respect to specific embodiments of the invention further below, the image information included in the shielded region may be used together with information about the X-ray absorption properties of the wedges, the position of the wedges, characteristics of the irradiated X-rays and/or characteristics of the object to be examined in order to calculate an artificial or virtual image corresponding to an X-ray image as if there were no wedges placed. In other words, an acquired X-ray image may be processed in a way such as to artificially remove the X-ray absorption of the wedges in the image. This virtual image may then be used for further automatic feature detection.

With such automatic wedge correction processing, the automatic wedge positioning can be made "dynamic" in a sense that it reacts on changes of a location of a region of interest within an X-ray image. The wedges may automatically follow the region of interest. It may not be necessary to provide other X-ray system information such as externally monitored movements of a patient or monitored displacement of a patient table in order to detect and continuously observe a region of interest motion.

In the following, possible features and advantages of embodiments of the present invention will be described in detail.

For acquiring an X-ray image of a region of interest of an object, a semitransparent transmitting device may be part of a collimator positioned within the beam of irradiating X-rays. The semitransparent X-ray transmitting device may be introduced laterally into the beam and may be moved such as to more or less extend into the beam thereby blocking or attenuating parts of the X-ray irradiation. The semitransparent X-ray transmitting device can have any arbitrary shape, material such as CuZn37 and material distribution. It may be advantageous to provide the semitransparent X-ray transmitting device as a wedge with linearly increasing thickness and with a homogeneous X-ray absorbing material. The semitransparent device may comprise one or more parts. For example, two or more wedges may be provided wherein each of the wedges may be displaced in a different direction perpendicular to the X-ray beam.

The X-ray absorption of the semitransparent X-ray transmitting device may vary within a range of 1 to 99%, preferably within a range of 20 to 95%. In other words, at an absorption level of 20%, 80% of the irradiated X-ray intensity is transmitted through the semitransparent device. Advantageously, the absorption properties of the semitransparent device are adapted such as to best possibly display a region of interest and blocking-out most of the examined object not belonging to the region of interest. Furthermore, the transition between these two extremes may be typically rendered smooth. Due to the fact that the device is semitransparent and not completely blocking to the incident X-rays, certain residual information remains detectable in the regions shielded by the semitransparent device. Residual information may be used to obtain suitable information for automatically adjusting the position of the semitransparent device.

It may be important to have precise information about X-ray absorption properties and in particular about the local variation of such X-ray absorption properties of the semitransparent X-ray transmitting device. For example, the semitransparent device can be adapted such that an X-ray absorption at an edge of the device, i.e. directly adjacent to a region of interest, is minimum whereas further distant from the edge, the X-ray absorption is increased. Knowledge about the local X-ray absorption properties may be used in order to advantageously derive image information included in the at least partly shielded regions of the acquired X-ray image in such a way that automatic feature detection may be performed on the acquired partly shielded X-ray image despite of image information loss within the partly shielded regions. Using this automatic feature detection, the position of the semitransparent device may be automatically re-adjusted.

According to an embodiment of the present invention, the image information included in the at least partly shielded regions on the detector surface is derived taking into account information on a predetermined position of the semitransparent X-ray transmitting device, characteristics of the irradiated X-rays and/or characteristics of the object to be examined. In order to be able to determine suitable image information included in the at least partly shielded regions for automatically adjusting the position of the semitransparent device, information on these specific characteristics may be used to at least partly compensate the image information loss due to the X-ray absorption within the semitransparent device.

For example, in one approach an image homogenisation techniques can be applied within the acquired image for example using some initial wedge positions to correct for the brightness differences between attenuated image areas and non-attenuated image area (for example: Rudin, S., Bednarek, D. R., Yang, C.-Y. J., *Real-time equalization of region-of-interest fluoroscopic images using binary masks*, Medical Physics 26:(7), page(s) 1359-1364, 1999, for example: Robert, N., Komljenovic, P. T., Rowlands, J. A., *A filtering method for signal equalization in region-of-interest fluoroscopy*, Medical Physics 29:(5), page(s) 736-747, 2002).

Another approach uses a wedge absorption model which may depend on information like the voltage and mAs of the X-ray source (defining the intensity of the X-ray source) and/or the type of a pre-filter and/or other system configurations which influence the x-ray dose on the detector. Such a wedge absorption model can be based on measurements of water plus wedge material as a function of the water and wedge thickness and all possible system settings. Such optionally calibrated wedge absorption model may calculate an original pixel value comprised in the at least partly shielded region on the detector surface based on the actual pixel value and the wedge thickness at the position of the pixel value. The quality of the virtual image as constructed by the wedge correction processing step should be sufficient for the feature detection algorithm, to detect again the region of interest in this virtual image. The necessary quality of the wedge correction processing step might depend on the quality of the feature detection algorithm and also the type of the feature to be detected and might be very application dependent.

According to a further embodiment of the present invention, the proposed image acquiring method further comprises a step of detecting a region of interest (ROI) wherein the position of the semitransparent X-ray transmitting device is adjusted to the detected region of interest. The region of interest may be e.g. a specific organ or a specific vessel structure within a patient. The region of interest may be an area irradiated by the X-rays and therefore comprised within the acquired X-ray image in which area the object of interest is comprised during the X-ray observation process. In case, the object of interest moves during the observation procedure such as for example in the case of a beating heart, the region of interest may be assumed as covering all possible positions at which the object of interest may be found during the observation. In case, the object of interest is static or moves only slowly, the region of interest may correspond to the outline of the object of interest and the position of the region of interest may follow the movement of the object of interest. Accordingly, the position of the semitransparent X-ray transmitting device may be automatically positioned such as to follow the position of the detected region of interest.

In order to detect a region of interest, a detection algorithm may be used to detect specific features of the object of interest. Such detection of features may be very application-specific. The feature detection may be based on a semi-automatic or even fully automatic image analysis. For example, specific visual features may be detected within the X-ray image.

In the specific example of cardiac interventions, the detection of a region of interest may comprise the estimate of a motion during a heart cycle and/or a respiratory cycle to ensure that the heart always remains within the non-shielded region of the acquired X-ray image. Furthermore, the motion can be continuously detected and estimated after the initial positioning of the semitransparent wedges and the position of the semitransparent wedges can be automatically adjusted to the motion of the heart.

According to a further embodiment of the present invention, a virtual image is generated from the acquired X-ray image wherein image information within the region partly shielded by the semitransparent X-ray transmitting device is re-established such as to correspond to image information with the semitransparent X-ray transmitting device absent. In other words, taking into account for example the X-ray absorption properties of the semitransparent device, the position of the semitransparent device, characteristics of the irradiated X-rays and/or characteristics of the observed object, a virtual image may be calculated which shows the entire content of the detection result of the X-ray detector in a way as if no semitransparent X-ray transmitting device would be positioned within the X-ray beam. Such virtual image may then be used for subsequent feature detection in order to detect a region of interest.

Alternatively, the detected region of interest by other system components or programs can be used as feature detection and provided to the unit which calculates the optimum wedge positions. For example the dose control unit might determine the patient region and excluding the direct radiation areas. This patient region can be provided to the automatic wedge positioning unit. In that case, it might be a direct link between the dose control unit and an automatic wedge positioning unit. Another example is the detection of a needle in an x-ray image in some application. The region around this needle might be provided to the automatic wedge positioning unit. In order that the feature detection steps follow the region of interest it might by necessary to include the wedge correction processing step before the feature detection unit, as mentioned above.

According to a further embodiment of the present invention, the steps of acquiring the X-ray image and adapting the position of the semitransparent X-ray transmitting device are repeated. Thereby, the position of the semitransparent X-ray transmitting device may be dynamically adjusted to a moving region of interest. The image acquisition and the position adaption of the semitransparent device may be repeated periodically. The repetition rate may be in a range of a few seconds or less than a second. Alternatively, the repetition rate may correspond to a rate of image acquisition during an X-ray observation procedure.

According to a further embodiment of the present invention, the semitransparent X-ray transmitting device comprises locally varying X-ray absorption properties. The step of adapting the position of the semitransparent X-ray transmitting device may then comprise displacing the semitransparent X-ray transmitting device laterally, for example perpendicularly, to the X-ray beam. In other words, for example a wedge-shaped semitransparent device may have an X-ray absorption increasing with an increasing thickness of the wedge. Accordingly, such wedge may be positioned close to a region of interest such that an X-ray absorption in the direct neighbourhood to the region of interest is minimum whereas X-ray absorption further apart is increased.

Summarizing and expressed in other words, features of the invention and its embodiments may be described as follows: Automatic wedge positioning is a method to determine an optimum position of semitransparent wedges based on some detected region of interest for an X-ray image acquisition device. Automatic feature detection algorithms may find the respective region of interest, calculate the optimal wedge position and move the collimators to the respective positions. However, after wedge placement, the feature detection may not be able to detect the feature any more. Examples are the cases of direct radiation or lung-field detection. It is therefore proposed to add a wedge correction step to correct the local wedge absorption in the image. This may result in an image as if there were no wedges placed. This corrected image may be then the input for the feature detection algorithm. In this way the automatic wedge positioning may be made dynamically in the sense that it may follow the region of interest and therefore may also follow feature movements or changes.

It has to be noted that features and advantages of the present invention have been described with reference to different embodiments of the invention. Particularly, features and advantages of the present invention are described herein with embodiments related to a method of acquiring an X-ray image or with respect to an X-ray image acquisition device. However, a person skilled in the art will gather from the above and the following description that, unless other notified, in addition to any combination or features belonging to one embodiment also any combinations of features relating to different embodiments considered to be disclosed herein.

BRIEF DESCRIPTION OF THE DRAWINGS

Features and advantages of the present invention will be further described with respect to specific embodiments as shown in the accompanying figures but to which the invention shall not be limited.

FIG. 1 shows an X-ray image acquisition device comprising automatic wedge positioning in accordance with an embodiment of the present invention.

The FIGURE is only schematical and not to scale.

DETAILED DESCRIPTION OF PREFERRED EMBODIMENTS

In order to generate an X-ray image of a body of a patient 13 positioned on a table 33, an X-ray image acquisition device 1 comprises an X-ray source 3 having an X-ray tube that generates an X-ray beam 35 directed towards the patient's body. The image acquisition device 1 comprises further an X-ray detector 5 that is adapted to measure with positional resolution an X-ray radiation transmitted through the body of the patient 13.

In order to restrict the emitted X-ray beam 35 to regions of the body of the patient 13 which comprise an object of interest, such as for example the cardiac vessels of a heart, the X-ray image acquisition device 1 further comprises a collimator 9 with a semitransparent X-ray transmitting device 11 provided as a wedge-shaped diaphragm. The wedges of the collimator 9 can be inserted into the X-ray beam 35. As the wedges are semitransparent to the irradiated X-rays, a portion 37 of the X-ray beam 35 is attenuated in X-ray intensity while another portion 39 of the X-ray beam 35 is transmitted in full intensity.

The X-ray beam 35 is transmitted through the patient's body and the transmitted X-ray intensity is then detected by the detector 5. From the detection result, information of X-ray absorption properties of the patient's body can be obtained. While the non-attenuated portion 39 of the X-ray beam 35 comprises maximum information about the body's absorption properties, the attenuated portion 37 of the X-ray beam 35 provides only reduced information. Accordingly, while the detection result within the region of the detector 5 in which the X-ray beam 35 has not been shielded by the collimator 9 comprises maximum intensity and mainly depends on the patient's body's X-ray absorption characteristics, the detection result in the at least partly shielded regions 17 on the detector surface 15 only have a strongly reduced detection result which furthermore also depends on the X-ray absorption properties of the semitransparent X-ray transmitting device 11.

The detection results of the X-ray detector 5 are provided to a control device 7. The control device 7 may, on the one hand, provide image signals to a display 27 such that a picture of a patient's organ 31 such as the heart may be displayed with special emphasis to a region of interest 29 such as cardiac vessels.

Furthermore, the control device 7 is adapted for determining and controlling an adjusted optimum position of the semitransparent X-ray transmitting device 11. For this purpose, the detection result from the detector 5 and optionally system settings (like kV, mAs, pre-filter type, source-detector-distance), obtained e.g. from a controller included in the X-ray source 3 or in the detector or in a separate controller device, may be provided to a detection device 21 which is adapted for detecting a feature determining a region of interest 29 within the image acquired by the detector 5.

In an initial processing step, the determined position of the region of interest may be used to determine an optimal positioning of the wedges within the collimator 9 such that portions 37 of the X-ray beam 35 outside of the region of interest are substantially attenuated.

In later steps of the X-ray observation proceedings, the detection results from the detector 5 and optionally system settings may be first provided to an analyzing unit 23. This analyzing unit 23 is adapted to generate a virtual image from the detected X-ray image. In this virtual image, the image information detected in the regions 17 of the detector surface 15 partly shielded by the collimator 9 is recalculated taking into account X-ray absorption properties of the collimator 9 such that the resulting virtual image corresponds to an X-ray image as if there was no X-ray attenuation within the collimator 9. This virtual image is then provided to the feature detection unit 21 for detecting the region of interest there from.

Having detected this region of interest which in the meantime may have been changed positionally, the automatic wedge positioning unit 25 is able to readjust the positioning of the semitransparent X-ray transmitting device 11.

For the calculation performed in the analysing unit 23 and/or the wedge positioning unit 25, it may be useful to also provide system settings (like kV, mAs, pre-filter type, source-detector-distance), obtained e.g. from a controller included in the X-ray source 3 or in the detector or in a separate controller device, to these units.

The image output by the control device 7 may be the incoming image from the detector or, alternatively, may be the virtual image generated by the wedge correction unit 23.

Finally, it should be noted that the terms "comprising", "including", etc. do not exclude other elements or steps and the terms "a" or "an" do not exclude a plurality of elements. Also, elements described in association with different embodiments may be combined. It should also be noted that reference signs in the claims should not be construed as limiting the scope of the claims.

LIST OF REFERENCE SIGNS

1 X-ray image acquisition device
3 X-ray source
5 X-ray detector
7 Control device
9 Collimator
11 Semitransparent X-ray transmitting device
13 Patient
15 Detector surface
17 Partly shielded regions on the detector surface
21 Feature detection device
23 Analyzing unit
25 Automatic wedge positioning unit
27 Display
29 Imaged region of interest
31 Imaged organ
33 Table

The invention claimed is:

1. An adaptable X-ray imaging apparatus comprising an X-ray source, an X-ray detector having a surface as an X-ray-receiving surface, and a semitransparent X-ray transmitting device, said apparatus configured for acquiring an image of a region of interest of an object by irradiating, via said source, X-rays to said object and detecting, on the detector surface, X-rays transmitted through said object, said apparatus further comprising an X-ray shielding processor configured for:
positioning said X-ray transmitting device into a beam of the irradiating X-rays so as to thereby at least partly shield regions on said detector surface from X-rays of said beam, and so as to provide on said surface, spatially separating ones of said regions, at another region, said another region being unshielded from X-rays of said beam;
acquiring, via said beam into which said X-ray transmitting device is positioned, an X-ray image by detecting X-rays transmitted through said object on said detector surface;
deriving, from the irradiated X-rays, image information included in the at least partly shielded regions on said detector surface; and
using the derived image information to automatically adjust the position of said X-ray transmitting device .

2. The apparatus of claim 1, wherein said image information is derived taking into account X-ray absorption properties of said X-ray transmitting device.

3. The apparatus of claim 1, wherein said image information is derived taking into account information on at least one of a predetermined position of said X-ray transmitting device, characteristics of the irradiated X-rays and characteristics of said object.

4. The apparatus of claim 1, further configured for detecting said region of interest, the adjusting comprising adjusting said position of said X-ray transmitting device to the detected region of interest.

5. The apparatus of claim 1, further configured for:
generating a virtual image from the acquired X-ray image, said generating comprising
re-establishing said image information such as to correspond to image information with said X-ray transmitting device absent.

6. The apparatus of claim 5, said X-ray transmitting device having locally varying X-ray absorption properties, the adjusting comprising displacing said X-ray transmitting device.

7. The apparatus of claim 1, further comprising a control device for the adjusting and a feature detection device, and configured for, via said feature detection device, detecting a feature determining said region of interest.

8. The apparatus of claim 1, said beam irradiating such that said regions exist concurrently with said another region.

9. The apparatus of claim 1, said X-ray transmitting device comprising two or more wedges displaced in different directions along a plane perpendicular to said beam.

10. A computer readable medium embodying a program for acquiring an image of a region of interest of an object by irradiating X-rays to said object and detecting, on a surface of an X-ray detector, X-rays transmitted through said object, said program having instructions executable by a processor for performing a plurality of acts, among said acts there being the acts of:
positioning a semitransparent X-ray transmitting device into a beam of the irradiating X-rays thereby at least partly shielding regions on the detector surface from X-rays;
acquiring, via said beam into which said device is position an X-ray image by detecting X-rays transmitted through said object on said detector surface;
deriving, from the irradiated X-rays, image information included in the at least partly shielded regions on said detector surface; and
using the derived image information to automatically adjust the position of said device,
said computer readable medium being further configured for, from said derived image information, generating a virtual image to correspond to an X-ray image as if there were no X-ray absorption by said device.

11. The computer readable medium of claim 10, said acquiring and the adjusting being repeated so as to dynamically re-adjust said position of said device to said detected region of interest.

12. An adaptable X-ray imaging apparatus for acquiring an image of a region of interest of an object by irradiating X-rays to the object and detecting, on a surface of an X-ray detector, X-rays transmitted through the object, said apparatus comprising an X-ray shielding processor configured for:
positioning a semitransparent X-ray transmitting device into a beam of the irradiating X-rays thereby at least partly shielding regions on the detector surface from X-rays;
continually acquiring an X-ray image by detecting X-rays transmitted, in a fixed direction, through said object on the detector surface;
deriving image information included in the at least partly shielded regions on said detector surface for dynamically correcting for movement of said region of interest within the continually acquired X-ray image; and,
for said correcting, automatically adjusting the position of said device based on said image information.

13. The apparatus of claim 12, said adjusting being performed such that imaging, via said beam, automatically follows said region of interest.

14. The apparatus of claim 13, said adjusting being performed such that said imaging continuously follows said region of interest.

15. The apparatus of claim 12, the adjusting being performed such that imaging to be acquired, via said beam, more fully corresponds with a virtual image.

16. The apparatus of claim 12, further comprising:
an X-ray source for said irradiating;
said X-ray detector; and
said device.

17. The apparatus of claim 12, further comprising a feature detection unit, said processor being further configured for providing a virtual image to said unit for detecting, from said virtual image, said region of interest.

18. The apparatus of claim 12, the continual acquiring being continuous such that said X-ray image is continuously acquired.

19. An X-ray image acquisition device for acquiring an image of a region of interest of an object by irradiating X-rays to the object and detecting on a detector surface X-rays transmitted through the object, said device comprising:
an X-ray source for generating an X- beam;
an adjustable semitransparent X-ray transmitting device positioned within a path of the X-ray beam;
an X-ray detector;
a feature detection device for detecting a feature determining a region of interest; and
a control device for adjusting a position of the semitransparent X-ray transmitting device;
wherein the X-ray image acquisition device is configured for:
positioning a semitransparent X-ray transmitting device into a beam of the irradiating X-rays thereby at least partly shielding regions on he detector surface from X-rays;
acquiring an X-ray image by detecting X-rays transmitted through the object on the detector surface;
automatically adusting the position of the semitransparent X-ray transmitting device based on image information included in the at least partly shielded regions on the detector surface; and
generating, from the said X-ray image acquired, a virtual image, said detecting being from said virtual image.

20. The X-ray image acquisition device of claim 19, said adjusting being responsive to said detecting of a feature determining a region of interest, said detecting of said feature and the responsive adjusting repeating automatically.

* * * * *